United States Patent [19]
de la Poterie et al.

[11] Patent Number: 5,972,354
[45] Date of Patent: *Oct. 26, 1999

[54] COMPOSITION INCLUDING A POLYMERIC SYSTEM AND USE OF SAID SYSTEM

[75] Inventors: Valérie de la Poterie, Le Chatelet En Brie; Isabelle Bara, Paris, both of France

[73] Assignee: L'Oreal, Paris, France

[ * ] Notice: This patent issued on a continued prosecution application filed under 37 CFR 1.53(d), and is subject to the twenty year patent term provisions of 35 U.S.C. 154(a)(2).

[21] Appl. No.: 08/742,584

[22] Filed: Oct. 28, 1996

[30] Foreign Application Priority Data

Oct. 27, 1995 [FR] France .................................. 95 12833
Feb. 14, 1996 [FR] France .................................. 95 01811

[51] Int. Cl.⁶ .............................. A61K 6/00; A61K 31/74
[52] U.S. Cl. .............................. 424/401; 424/59; 424/63; 424/64; 424/78.02; 424/78.03; 424/400; 424/118.08; 514/844; 514/845; 514/937; 514/772
[58] Field of Search .............................. 424/78.02, 78.03, 424/401, 59, 63, 64, 400, 118.08; 514/844, 845, 937, 772

[56] References Cited

U.S. PATENT DOCUMENTS 4,988,502  1/1991  Ounanian et al. .

FOREIGN PATENT DOCUMENTS

| | | |
|---|---|---|
| 0 140 325 | 5/1985 | European Pat. Off. . |
| 0 206 671 | 12/1986 | European Pat. Off. . |
| 0 530 084 | 3/1993 | European Pat. Off. . |
| 0 566 442 | 10/1993 | European Pat. Off. . |
| 0 581 581 | 2/1994 | European Pat. Off. . |
| 0 628 304 | 12/1994 | European Pat. Off. . |
| 0 636 361 | 2/1995 | European Pat. Off. . |
| 0 637 600 | 2/1995 | European Pat. Off. . |
| 0 655 234 | 5/1995 | European Pat. Off. . |
| 2 238 242 | 5/1991 | United Kingdom . |
| WO 91/12793 | 9/1991 | WIPO . |

OTHER PUBLICATIONS

Patent Abstracts of Japan, vol. 10, No. 383, JP–A–61 176512 (Dec. 1986).

Patent Abstracts of Japan, vol. 13, No. 308, JP–A–01 096110 (Jul. 1989).

Chemical Abstracts, vol. 89, No. 22, 89:185917h, (Nov. 1978).

Chemical Abstracts, vol. 97, No. 18, 97:150584k, (Nov. 1982).

*Primary Examiner*—Bernard Lipman
*Assistant Examiner*—N. Sarofim
*Attorney, Agent, or Firm*—Finnegan, Henderson, Farabow, Garrett & Dunner, L.L.P.

[57] ABSTRACT

This patent application relates to a composition capable of being applied to the skin and/or the mucosae, including a polymeric system which includes an aqueous dispersion of particles of film-forming polymer, the said polymeric system making it possible to obtain a supple and flexible film. The invention also relates to the use of such a polymeric system in such an, especially cosmetic, composition.

51 Claims, No Drawings

COMPOSITION INCLUDING A POLYMERIC SYSTEM AND USE OF SAID SYSTEM

The present invention relates to a composition, especially a cosmetic composition, capable of being applied to the skin, the semimucosae and/or the mucosae. The composition includes in particular an aqueous dispersion of particles of film-forming polymer and can be employed as a make-up product.

Compositions to be applied to the skin, the semimucosae and/or the mucosae, such as lipsticks and foundations are generally in the form of a stick, of flexible paste or of cast paste, and include fatty substances such as oils, pasty compounds and/or waxes and a particulate phase generally made up of fillers and pigments.

When applied to the skin, the mucosae or the semimucosae, however, these compositions exhibit the disadvantage of transferring. What this means is that the composition is capable of being deposited, at least partially, on some supports with which it is brought into contact, such as, for example, a glass, a cup, a garment or the skin. By being deposited, the composition leaves a mark on the support. This therefore results in a mediocre persistence of the composition on the skin, the semimucosae or the mucosae, and the need to reapply it regularly.

Furthermore, the appearance of unacceptable marks on some garments and especially on blouse collars can discourage some people from using make-up of this type.

Another disadvantage of these compositions lies in the problem of migration. It has been found, in fact, that some compositions tend to propagate inside small wrinkles and/or wrinkles of the skin, in the case of foundations; in the small wrinkles which surround the lips, in the case of lipsticks, and in the folds of the eyelid in the case of eyeshadows. It has also been found, especially in the case of eyeshadows, that streaks appear in the make-up, which are generated by the movements of the eyelids. It has further been found that eyeliners can also run.

All these phenomena produce an unaesthetic effect which is quite desirable to avoid.

For a number of years many cosmeticians have been interested in cosmetic compositions, especially lipsticks or blushers which are "transfer-free". "Transfer-free" lipstick compositions have thus been envisaged containing from 1 to 70% by weight of liquid silicone resin with silicate repeat units, from 10 to 98% by weight of a volatile silicone oil and pulverulent fillers. However, the film obtained on the lips after evaporation of the silicone oil has the disadvantage of becoming uncomfortable in the course of time (a feeling of drying out and of tightness).

"Transfer-free" lipsticks are also known, containing a volatile silicone and a silicone resin comprising a pendent esterified chain which has at least 12 carbon atoms. The film of lipstick can disadvantageously be uncomfortable when applied, and in particular can be too dry.

In general, the combination of volatile oils with some silicone-containing compounds makes it possible to obtain a satisfactory "transfer-free" result. However, the films obtained after application of these compositions and evaporation of the volatiles nevertheless have the disadvantage of being relatively matte and thus produce a make-up which is not very glossy.

A need continues, therefore, to exist for a cosmetic composition which does not substantially transfer, i.e., does not transfer much or does not do so at all, that is to say a "transfer-free" composition, but which also possesses good cosmetic properties, and in particular makes it possible to obtain a film which can be, at will, more or less glossy.

A preferred objective of the present invention is a composition which makes it possible to obtain a film which behaves very well, which does not substantially transfer, which does not substantially stain a support with which it might be in contact, and which does not substantially migrate in the course of time, while making it possible to obtain a make-up and/or a glossy film.

Thus, a subject of the present invention is the use, in a composition capable of being applied to the skin, the semimucosae and/or the mucosae, of a polymeric system or a composition including the polymeric system including an aqueous dispersion of particles of film-forming polymer, the system making it possible to obtain a film which has an elongation greater than or equal to approximately 200%. The elongation is preferably from 200% to 10,000%, and more preferably from 200% to 5,000%

Another subject of the invention is the use of a polymeric system or of a composition including it for making-up, protecting and/or treating nontherapeutically and/or for the manufacture of a composition intended for treating therapeutically the skin, the semimucosae and/or the mucosae, in particular the lips, this system including an aqueous dispersion of particles of film-forming polymer and making it possible to obtain a film which has an elongation greater than or equal to approximately 200%, and preferably a film with very good behaviour and/or which does not substantially transfer and/or which does not substantially migrate and/or which does not substantially stain; and/or in order to obtain a supple and/or elastic and/or flexible film on the skin and/or a film which follows the movements of the skin and/or does not substantially crack up and/or does not substantially lift off; and/or in order to obtain a glossy film.

Another subject of the invention is a composition capable of being applied to the skin, the semimucosae and/or the mucosae, including a polymeric system which includes an aqueous dispersion of particles of film-forming polymer, this system making it possible to obtain a film which has an elongation greater than or equal to approximately 200%.

Another subject of the invention is a transfer-free lipstick composition including a polymer system which includes an aqueous dispersion of particles of film-forming polymer, in which the polymeric system makes it possible to obtain a film which has an elongation greater than or equal to approximately 200%. It has been found that the composition according to the invention can be applied with ease and spreads easily and uniformly on the skin, the semimucosae and the mucosae, in particular on the lips.

The composition according to the invention namely finds an application which is particularly advantageous in the field of the care and/or the make-up of the skin, of the mucosae and/or of the semimucosae. The mucosae are intended to mean especially the inner part of the lower eyelid; the meaning of the semimucosae is intended to include more particularly the lips.

A preferred composition according to the invention makes it possible to obtain a homogeneous film which has a light texture and remains comfortable to wear all day long. The film is preferably not at all sticky, while being soft, supple, elastic and flexible on the skin; it follows the movements of the skin without substantially cracking up and/or coming off. It preferably adheres substantially completely to the skin and especially to the lips.

The composition according to the invention therefore finds a particular application as a composition for application to the lips, especially as lipstick.

Furthermore the film obtained can be very glossy or more or less matte, depending on the nature of the constituents of the composition, resulting in a wider range of make-up products which are glossy or matte at will.

The composition according to the invention therefore includes a polymeric system which includes at least one aqueous dispersion of particles of film-forming polymer. Among the film-forming polymers that can be employed within the scope of the present invention may be mentioned synthetic polymers of the polycondensate type or of the radical type, polymers of natural origin and mixtures thereof.

Thus, among the polycondensates there may be mentioned anionic, cationic, nonionic or amphoteric polyurethanes, acrylic polyurethanes, polyvinylpyrrolidone polyurethanes, polyester polyurethanes, polyether polyurethanes, polyureas, polyurea/polyurethanes and mixtures thereof.

The polyurethane may be, for example, a polyurethane copolymer, polyurea/urethane or polyurea, which is aliphatic, cycloaliphatic or aromatic, comprising, by itself or as a mixture,

- at least one block originating from linear or branched aliphatic and/or cycloaliphatic and/or aromatic polyester, and/or
- at least one block originating from aliphatic and/or cycloaliphatic and/or aromatic polyether, and/or
- at least one silicone-containing block, substituted or otherwise, branched or otherwise, for example polydimethylsiloxane or polymethylphenylsiloxane, and/or
- at least one block comprising fluorine-containing groups.

The polyurethanes as defined in the invention may also be obtained from polyesters, branched or otherwise, or from alkyds comprising mobile hydrogens which are modified by reaction with a diisocyanate and a difunctional (for example dihydro-, diamino-, or hydroxyamino-) organic compound, additionally comprising either a carboxylic acid or carboxylate group or a sulphonic acid or sulphonate group, or else a neutralizable tertiary amine group or a quaternary ammonium group.

Polyesters, polyesteramides, polyesters containing a fatty chain, polyamides and epoxy ester resins may also be mentioned.

The polyesters may be obtained, in a known manner, by polycondensation of aliphatic or aromatic diacids with aliphatic or aromatic diols or polyols. Succinic acid, glutaric acid, adipic acid, pimelic acid, suberic acid or sebacic acid may be employed as aliphatic diacids. Terephthalic acid or isophthalic acid, or else a derivative such as phthalic anhydride, may be employed as aromatic diacids. Ethylene glycol, propylene glycol, diethylene glycol, neopentyl glycol, cyclohexanedimethanol and 4,4'-(1-methyl propylidene)bisphenol may be employed as aliphatic diols. Glycerol, pentaerythritol, sorbitol and trimethylolpropane may be employed as polyols.

The polyesteramides may be obtained in a similar manner to the polyesters, by polycondensation of diacids with diamines or aminoalcohols. Ethylenediamine, hexamethylenediamine and meta- or para-phenylenediamine may be employed as a diamine. Monoethanolamine may be employed as a aminoalcohol.

As monomer carrying an anionic group capable of being employed during the polycondensation there may be mentioned, for example, dimethylolpropionic acid, trimellitic acid or a derivative such as trimellitic anhydride, the sodium salt of 3-sulphopentanediol acid and the sodium salt of 5-sulpho-1,3-benzenedicarboxylic acid.

Polyesters containing a fatty chain can be obtained by the use of diols containing a fatty chain during the polycondensation.

Epoxy ester resins can be obtained by polycondensation of fatty acids with a condensate containing $\alpha,\omega$-diepoxy ends.

Polymers of radical type can be especially acrylic and/or vinyl polymers or copolymers. Anionic radical polymers are preferably employed.

As monomer carrying an anionic group capable of being employed during the radical polymerization there may be mentioned acrylic acid, methacrylic acid, crotonic acid, maleic anhydride and 2-acrylamido-2-methylpropanesulphonic acid.

The acrylic polymers can result from the copolymerization of monomers chosen from esters and/or amides of acrylic acid or of methacrylic acid. Examples of monomers of ester type which may be mentioned are methyl methacrylate, ethyl methacrylate, butyl methacrylate, isobutyl methacrylate, 2-ethylhexyl-methacrylate and lauryl methacrylate. N-t-Butylacrylamide and N-t-octylacrylamide may be mentioned as examples of monomers of amide type.

Acrylic polymers are preferably employed which are obtained by copolymerization of monomers containing ethylenic unsaturation containing hydrophilic groups, preferably of nonionic nature, such as hydroxyethyl acrylate, 2-hydroxypropyl acrylate, hydroxyethyl methacrylate and 2-hydroxypropyl-methacrylate.

The vinyl polymers may result from the homopolymerization or copolymerization of monomers chosen from vinyl esters, styrene and butadiene. Examples of vinyl esters which may be mentioned are vinyl acetate, vinyl neodecanoate, vinyl pivalate, vinyl benzoate and vinyl t-butylbenzoate.

It is also possible to employ acrylic/silicone copolymers or nitrocellulose/acrylic copolymers.

Polymers of natural origin, optionally modified, may be chosen from shellac resin, gum sandarac, dammars, elemis, copals, cellulose derivatives and mixtures thereof.

There may also be mentioned the polymers resulting from the radical polymerization of one or more radical monomers inside and/or partially at the surface of preexisting particles of at least one polymer chosen from the group consisting of polyurethanes, polyureas, polyesters, polyesteramides and/ or alkyds. These polymers are generally called hybrid polymers.

The aqueous dispersion including one or more filmforming polymers, can be prepared by a person skilled in the art on the basis of his or her general knowledge. Aqueous dispersions providing the desired degree of elongation are known in the art and can be made, for example, by the techniques disclosed in EP-A-0 655 234, EP-A-0 530 084, EP 0 628 304, EP 0 636 361, and EP 0 637 600, the disclosures of which are incoporated by reference herein.

In order to improve the film-forming nature of a polymer, for example by lowering its glass transition temperature, a coalescing agent, which may be chosen from known coalescing agents, may be added to the dispersion. In the present description "dispersion of film-forming polymer" is intended to mean a dispersion capable of forming a film, including or not including a coalescing agent.

The solids content of the said aqueous dispersions according to the present invention may be of the order of 5–60% by weight, and preferably 30–40%.

The composition may include 1–60% by weight, preferably 5–40% by weight, of dry solids of film-forming polymers.

The particle size of the polymers in aqueous dispersion may preferably be from 10 to 500 nm and is more preferably from 20 to 150 nm, and this makes it possible to obtain a film which has a remarkable gloss.

To carry out the present invention, the polymeric system must make it possible to obtain a film on the support onto which it is deposited, the film having an elongation greater than or equal to approximately 200%.

To this end, the polymeric system includes an aqueous dispersion of particles of film-forming polymer. When the dispersion of polymer particles does not make it possible, by itself, to obtain a film which has an elongation greater than or equal to approximately 200%, then it is possible to add a compound, the function of which is to modify the elongation of the film in the desired manner.

Such an elongation-modifying compound will be called a "plasticizing agent" herein. The polymeric system then includes the dispersion of particles of film-forming polymer and the plasticizing agent.

The plasticizing agent can be chosen from among all the compounds known to a person skilled in the art as being capable of fulfilling the required function. This agent may be water-soluble or water-insoluble and may optionally be in the form of an aqueous dispersion.

The usual plasticizing agents, such as the following, may be mentioned in particular, by themselves or as a mixture:

glycols and their derivatives, such as diethylene glycol ethyl ether, diethylene glycol methyl ether, diethylene glycol butyl ether or diethylene glycol hexyl ether, ethylene glycol ethyl ether, ethylene glycol butyl ether, and ethylene glycol hexyl ether, glycerol esters, propylene glycol derivatives and in particular propylene glycol phenyl ether, propylene glycol diacetate, dipropylene glycol butyl ether, tripropylene glycol butyl ether, propylene glycol methyl ether, dipropylene glycol ethyl ether, tripropylene glycol methyl ether, diethylene glycol methyl ether, and propylene glycol butyl ether, esters of acids, especially carboxylic ones, such as citrates, phthalates, adipates, carbonates, tartrates, phosphates, sebacates, oxyethylenated derivatives, such as oxyethylenated oils, especially vegetable oils, such as castor oil, and silicone oils, polymers which are water-soluble or in aqueous dispersion, which have a low glass transition temperature, lower than 25° C., preferably lower than 15° C.

The quantity of plasticizing agent is chosen by the person skilled in the art on the basis of his or her general knowledge, so as to obtain a polymeric system resulting in a film which has an elongation greater than or equal to approximately 200%, while preserving the cosmetically acceptable properties of the composition.

The composition according to the invention therefore includes a polymeric system which includes an aqueous dispersion of particles of film-forming polymer, the system making it possible to obtain a film which has an elongation greater than or equal to approximately 200%. The elongation may be preferably greater than 300%.

The elongation is measured according to the standard ASTM Standards, volume 06.01 D 2370-92 "Standard Test Method for Tensile Properties of Organic Coatings".

The composition may additionally include at least one water-soluble dye and/or at least pigment, which are employed in a manner which is conventional in the field of cosmetics and make-up.

Pigments should be understood to mean inorganic or organic, white or coloured, particles which are insoluble in the medium and are intended to colour and/or to opacify the composition. The pigments may be present in the composition in a proportion of 0–20% by weight of the final composition and preferably in a proportion of 1–5%. They may be white or coloured, inorganic and/or organic, of usual or nanometre size.

Among the inorganic pigments and/or nanopigments may be mentioned titanium, zirconium or cerium dioxide and zinc, iron or chromium oxides and ferric blue. Among organic pigments may be mentioned carbon black and barium, strontium, calcium and aluminium lakes.

Among the water-soluble dyes may be mentioned Ponceau disodium salt, Alizarin Green disodium salt, quinoline yellow, amaranth trisodium salt, tartrazine disodium salt, rhodamine monosodium salt, fuchsin disodium salt, xanthophyll and mixtures thereof.

Any known additive may also be added to the composition according to the invention, such as thickening agents, for example clays, gums, silicas, cellulose derivatives, a synthetic polymer such as an acrylic polymer or an associative polymer of polyurethane type, a natural gum such as xanthan gum, spreading agents, dispersants, antifoaming agents, wetting agents, UV filters, perfumes, fillers, cosmetic or pharmaceutical active substances, hydrating agents, vitamins and their derivatives, and biological substances and their derivatives.

A person skilled in the art will, of course, take care to select these optional additives and/or their quantity in such a way that the advantageous properties of the composition according to the invention are not, or are not substantially, impaired by the envisaged addition.

The pH of the final composition obtained is preferably lower than 9. This composition must, of course, be capable of being deposited on a support such as the skin, the semimucosae or the mucosae.

The composition according to the invention may be in a fluid, gel, semisolid, flexible paste or even solid form such as a stick or rod.

It finds an application in particular as product for make-up, especially as lipstick, foundation, cheek blusher or eyeshadow or eyeliner. An application may also be envisaged in the field of care compositions, sun or tanning compositions, dermatological compositions or pharmaceutical compositions to be applied to the skin, the semimucosae and/or the mucosae.

The invention is illustrated in greater detail in the following examples, which are not intended to limit the invention.

EXAMPLE 1

Aqueous dispersions of various film-forming polymers were prepared, the dispersions making it possible to obtain films which have a variety of elongations.

The composition was deposited on a support so as to form a film.

The elongation of the film obtained was measured and the behaviour of the film on the lips was assessed.

The following results were obtained, with Polyurethane 1 being comparative and the others being useful in the presently disclosed invention:

| Polymer | Elongation | Visual assessment |
| --- | --- | --- |
| Polyurethane 1: SANCURE 2060 | 120% | cracks ver quickly in the middle of the lips; lifts off quickly on the sides |

-continued

| Polymer | Elongation | Visual assessment |
| --- | --- | --- |
| Polyurethane 2: SANCURE 815 | 200% | cracks a little; lifts off after some time |
| Polyurethane 3: NEOREZ R-974 | 280% | cracks a little; lifts off after some time |
| Polyurethane 4: NEOREZ R-981 | 330% | long time to crack; does not lift off |
| Polyurethane 5: SANCURE 878 | 425% | very long time to crack; does not lift off |
| Polyurethane 6: SANCURE 2255 | 550% | very long time to crack; does not lift off |
| Polyurethane 7: SANCURE 861 | 580% | does not crack; very supple |

SANCURE polymers are available commercially from Sanncor Co. NEOREZ polymers are available commercially from ICI.

It has therefore been found, based on the above tests, that a suitable film which behaves well and is relatively supple is obtained when the polymer makes it possible to obtain a film which has an elongation greater than or equal to 200%, preferably greater than 300%, more preferably greater than 400%.

EXAMPLE 2

An eyeliner was prepared which had the following composition:
aqueous dispersion of polyurethane 95 g
(elongation 580%)
pigment 2 g
plasticizing agent (glycerine) 1.25 g A composition was obtained which was easy to apply to the outline of the eye, which gave a satiny line and which did not transfer or run.

EXAMPLE 3

A lipstick which had the following composition was prepared:
aqueous dispersion of polyurethane 95 g
(elongation 330%)
pigment 1 g
plasticizing agent (glycerine) 1.25 g A composition was obtained which was easy to apply to the lips; the film obtained was glossy; it did not transfer or migrate into small wrinkles; it resisted well and followed the movement of the lips.

EXAMPLE 4—(comparative example)

A lipstick was prepared which had the following composition:
aqueous dispersion of polyurethane 95 g
(elongation 120%)
pigment 1 g
plasticizing agent (glycerine) 1.25 g A film was obtained which cracked very rapidly after it had been applied to the lips.

What is claimed is:

1. A method for making up, protecting, or treating the skin, semimucosae or mucosae, said method comprising the step of applying to said skin, semimucosae or mucosae a polymeric system or a composition including said polymeric system, wherein said polymeric system comprises an aqueous dispersion of particles of at least one film-forming polymer sufficient to produce a film upon application which has an elongation greater than or equal to approximately 200%.

2. A method according to claim 1, wherein said semimucosae are the lips.

3. A method according to claim 1, wherein said film does not substantially transfer, migrate, or stain.

4. A method according to claim 1, wherein said film obtained is supple, elastic, and flexible on the skin, follows the movements of the skin, substantially does not crack, and substantially does not lift off.

5. A method according to claim 1, wherein said film is a glossy film.

6. A method according to claim 1, wherein said composition is a make-up composition, a care composition, a sun or tanning composition, a dermatological composition, or a pharmaceutical composition.

7. A method according to claim 6, wherein said make-up composition is a lipstick, a foundation, a blusher, an eyeshadow, or an eyeliner composition.

8. A method according to claim 1, wherein said elongation is greater than approximately 300%.

9. A method according to claim 1, wherein the film-forming polymer is selected from anionic, cationic, nonionic and amphoteric polyurethanes, polyesters, polyesteramides, polyamides, epoxy ester resins, vinyl polymers and their copolymers, optionally modified polymers of natural origin, and polymers resulting from the radical polymerization of one or several radical monomers inside or partially at the surface of preexisting particles of at least one polymer selected from polyurethanes, polyureas, polyesters, polyesteramides, alkyds, and mixtures thereof.

10. A method according to claim 9, wherein said anionic, cationic, nonionic and amphoteric polyurethanes are acrylic polyurethanes, polyvinylpyrrolidone polyurethanes, polyester polyurethanes, polyether polyurethanes, polyureas, or polyurea/polyurethanes.

11. A method according to claim 9, wherein said polyesters are polyesters containing a fatty chain.

12. A method according to claim 9, wherein said vinyl polymers and their copolymers are acrylic polymers and copolymers.

13. A method according to claim 12, wherein said acrylic copolymers are acrylic/silicone copolymers or nitrocellulose/acrylic copolymers.

14. A method according to claim 1, wherein the size of the polymer particles in aqueous dispersion is from 10 to 500 nm.

15. A method according to claim 14, wherein the size of the polymer particles in aqueous dispersion is from 20 to 150 nm.

16. A method according to claim 1, wherein the polymeric system additionally includes at least one plasticizing agent.

17. A method according to claim 16, wherein said at least one plasticizing agent is selected from glycols and their derivatives, glycerol esters, propylene glycol derivatives, esters of acids, oxyethylenated derivatives, and polymers which are water-soluble or in aqueous dispersion, said polymers having a glass transition temperature lower than 25° C.

18. A method according to claim 17, wherein said at least one plasticizing agent is selected from carboxylic acid esters.

19. A method according to claim 17, wherein said at least one plasticizing agent is selected from polymers which are water-soluble or in aqueous dispersion, which have a glass transition temperature lower than 15° C.

20. A composition for application to the lips, said composition including a polymeric system, wherein said polymeric system comprises an aqueous dispersion of particles of at least one film-forming polymer sufficient to produce a film upon application which has an elongation greater than or equal to approximately 200%, and which is able to follow the movement of the lips.

21. A composition according to claim 20, wherein said film does not substantially transfer, migrate, or stain.

22. A composition according to claim 20, wherein said film is a glossy film.

23. A composition according to claim 20, wherein said composition is in the form of a make-up composition, a dermatological composition, or a pharmaceutical composition.

24. A composition according to claim 20, wherein said composition is in the form of a lipstick.

25. A composition according to claim 20, wherein said elongation is greater than approximately 300%.

26. A composition according to claim 20, wherein the film-forming polymer is selected from anionic, cationic, nonionic and amphoteric polyurethanes polyesters, polyesteramides, polyamides, epoxy ester resins, vinyl polymers and their copolymers, optionally modified polymers of natural origin, and polymers resulting from the radical polymerization of one or several radical monomers inside or partially at the surface of preexisting particles of at least one polymer selected from polyurethanes, polyureas, polyesters, polyesteramides, alkyds, and mixtures thereof.

27. A composition according to claim 26, wherein said anionic, cationic, nonionic and amphoteric polyurethanes are acrylic polyurethanes, polyvinylpyrrolidone polyurethanes, polyester polyurethanes, polyether polyurethanes, polyureas, or polyurea/polyurethanes.

28. A composition according to claim 26, wherein said polyesters are polyesters containing a fatty chain.

29. A composition according to claim 26, wherein said vinyl polymers and their copolymers are acrylic polymers and copolymers.

30. A composition according to claim 29, wherein said acrylic copolymers are acrylic/silicone copolymers or nitrocellulose/acrylic copolymers.

31. A composition according to claim 20, wherein the size of the polymer particles in aqeuous dispersion is from 10 to 500 nm.

32. A composition according to claim 31, wherein the size of the polymer particles in aqeuous dispersion is from 20 to 150 nm.

33. A composition according to claim 20, wherein said polymeric system additionally includes at least one plasticizing agent.

34. A composition according to claim 33, in which said at least one plasticizing agent is selected from glycols and their derivatives, glycerol esters, propylene glycol derivatives, esters of acids, oxyethylenated derivatives, and polymers which are water-soluble or in aqueous dispersion, which have a glass transition temperature lower than 25° C.

35. A composition according to claim 34, wherein said at least one plasticizing agent is selected from carboxylic acid esters.

36. A composition according to claim 34, wherein said at least one plasticizing agent is selected from polymers which are water-soluble or in aqueous dispersion, which have a glass transition temperature lower than 15° C.

37. A composition according to claim 20, including at least one additional ingredient selected from water-soluble dyes and pigments.

38. A transfer-free lipstick composition including a polymeric system, wherein said polymeric system comprises an aqueous dispersion of particles of at least one film-forming polymer sufficient to produce a film upon application which has an elongation greater than or equal to approximately 200%.

39. A method according to claim 1, wherein the elongation of said film ranges from 200% to 10,000%.

40. A method according to claim 39, wherein the elongation of said film ranges from 200% to 5,000%.

41. A composition according to claim 20, wherein the elongation of said film ranges from 200% to 10,000%.

42. A composition according to claim 41, wherein the elongation of said film ranges from 200% to 5,000%.

43. A method of preparing a transfer-free lipstick composition comprising the step of including in said lipstick composition an effective amount of a polymeric system, wherein said polymeric system comprises an aqueous dispersion of particles of at least one film-forming polymer sufficient to produce a film upon application which has an elongation greater than or equal to approximately 200%.

44. A method of producing a film of a transfer-free lipstick composition, said film having an elongation greater than or equal to approximately 200%, said method comprising the steps of:
  applying to the lips a transfer-free lipstick composition, wherein said lipstick composition includes an effective amount of a polymeric system, wherein said polymeric system comprises an aqueous dispersion of particles of at least one film-forming polymer; and
  allowing said composition to remain on the lips for a time sufficient to form said film.

45. An eyeliner composition, said composition including a polymeric system, wherein said polymeric system comprises an aqueous dispersion of particles of at least one film-forming polymer sufficient to produce a film upon application which has an elongation greater than or equal to approximately 200%, and which is able to follow the movement of the skin around the eyes.

46. A skin make-up composition, said composition including a polymeric system, wherein said polymeric system comprises an aqueous dispersion of particles of at least one film-forming polymer sufficient to produce a film upon application which has an elongation greater than or equal to approximately 200%, and which is able to follow the movement of the skin around the eyes.

47. A composition according to claim 20, wherein said at least one film forming polymer is present in an amount ranging from 1 to 60% by weight of dry solids of film forming polymer.

48. A composition according to claim 47, wherein said at least one film forming polymer is present in an amount of at least 5% by weight of dry solids of film forming polymer.

49. A composition according to claim 48, wherein said at least one film forming polymer is present in an amount ranging from 5 to 40% by weight of dry solids of film forming polymer.

50. A composition according to claim 20, further comprising a pigment in an amount ranging from 0 to 20% by weight of the final composition.

51. A composition according to claim 50, wherein the ratio of said pigment to said at least one film-forming polymer is less than 1.

* * * * *